United States Patent
Kostuck

[11] Patent Number: 5,976,461
[45] Date of Patent: Nov. 2, 1999

[54] METHOD FOR PROTECTING COOLING WATER SYSTEMS

[76] Inventor: Paul R. Kostuck, N3289 Laural Rd., Lake Geneva, Wis. 53147

[21] Appl. No.: 09/072,655

[22] Filed: May 5, 1998

[51] Int. Cl.$^6$ .................................................. G01N 35/08
[52] U.S. Cl. .............................. 422/7; 422/40; 422/105; 422/107; 422/114; 73/53.01; 137/487.5; 165/11.1; 165/70; 210/85; 210/96.1; 210/739
[58] Field of Search .............................. 422/7, 40, 8–19, 422/105, 107, 114; 210/85, 96.1, 739; 73/53.01; 165/11.1, 70; 137/487.5

[56] References Cited

U.S. PATENT DOCUMENTS

| | | | |
|---|---|---|---|
| 4,103,536 | 8/1978 | Chipman | 73/40 |
| 4,547,294 | 10/1985 | Goeldner | 210/697 |
| 4,992,380 | 2/1991 | Moriarty et al. | 436/55 |
| 5,266,493 | 11/1993 | Young | 436/55 |
| 5,296,196 | 3/1994 | Takeshima | 422/98 |
| 5,341,128 | 8/1994 | Keyser et al. | 340/605 |
| 5,514,338 | 5/1996 | Simon et al. | 422/82.02 |

Primary Examiner—Terrence R. Till
Assistant Examiner—Fariborz Moazzam
Attorney, Agent, or Firm—Chase & Yakimo, L.C.

[57] ABSTRACT

A method for protecting cooling water systems from corrosion is disclosed which monitors the hydrocarbon concentration in a cooling fluid flow and activates protective procedures upon detection of a predetermined concentration. According to the method, a fluid flow of cooling water from a cooling tower is directed through an upstream gate valve before entering a heat exchange apparatus where heat from an industrial process fluid flow is transferred to the cooling fluid flow. The hydrocarbon concentration of the heated cooling fluid flow is monitored as it is directed out of the heat exchange apparatus for return to a cooling tower. However, if a concentration of hydrocarbons is detected in the fluid flow which indicates possible process fluid leakage, upstream and downstream cooling fluid gate valves as well as a process fluid gate valve are automatically closed. Gate closure prevents additional process fluid leakage and prevents polluted cooling fluid flow from contaminating the system by returning to the cooling tower for recirculation. Thus, a heat exchange apparatus which is introducing impurities into the cooling water system can be isolated and repaired while the remainder of the system continues to operate.

8 Claims, 5 Drawing Sheets

METHOD FOR PROTECTING COOLING WATER SYSTEMS

BACKGROUND OF THE INVENTION

This invention relates to cooling water systems and, more particularly, to a method for protecting cooling water systems from contamination by monitoring hydrocarbon concentrations within a flowing aqueous solution and activating alarms or shutdown procedures accordingly.

Cooling towers are devices frequently used in chemical, refining, and power production industries for cooling a liquid, typically water, which has become heated as a result of being circulated about a hot fluid stream such as petroleum products. Following this heat exchange, the heated water is returned to the cooling tower where it is exposed to an upward air stream to facilitate cooling prior to recirculation. Impurities in industrial cooling waters is a significant problem which may lead to scaling, fouling, and corrosion of heat exchange equipment, pipelines, or the cooling tower itself. Consequently, these problems result in economic disadvantages such as early replacement of equipment, energy waste due to decreased heat transfer efficiency, extended or unscheduled downtime, and environmental pollution through evaporation of impure cooling water. Impurities such as hydrocarbons often enter the cooling water system through leakage of process fluids such as petroleum products during the heat exchange process.

Various methods and devices have been proposed in the prior art for detecting the presence of hydrocarbons in a reservoir of water such as a cooling tower or testing vessel. Although assumably effective in operation, such known methods and devices require periodic human assessments of water purity before the industrial process may be halted to prevent damage to equipment or the environment. Further, other known methods merely add corrosion inhibiting chemicals to the cooling waters for protecting equipment without identifying the source of the impurity for corrective purposes.

Thus, it is desirable to have a method for continuously monitoring circulating cooling waters for the presence of impurities within a cooling water system. It is also desirable to have a method for monitoring cooling waters which automatically halts circulation of both the process and cooling streams within the polluted segment of the system upon sensing a predetermined impurity level.

SUMMARY OF THE INVENTION

In response thereto, I have invented a method for protecting cooling water systems which utilizes one or more hydrocarbon sensors for detecting impurities such as hydrocarbons circulating within the cooling water system. A hydrocarbon sensor is mounted to each cooling water pipe for detecting hydrocarbons which is indicative of process fluid leakage into the cooling water during heat exchange.

Water cooled by a cooling tower is pumped through water pipes into heat exchange units, the water passing through one or more upstream gate valves. Fluids heated during the industrial process are simultaneously channeled through other upstream gate valves into the heat exchange units. Within the heat exchange units, cooling water is disbursed about the heated process fluid pipeline, thereby facilitating a transfer of heat from the process fluids to the cooling water. The heated water is then channeled into downstream pipelines for return to the cooling tower for cooling and recirculation. As heated water leaves a heat exchange unit, a hydrocarbon sensor monitors the water for the presence of hydrocarbon molecules and calculates the percentage concentration in parts per million (ppm).

If a predetermined concentration of hydrocarbons is detected, the sensor apparatus initiates closure of the appropriate upstream and downstream cooling stream gate valves and upstream process line gate valve. The sensor apparatus simultaneously sends a signal to a central control panel which activates audio and visual alarms. Accordingly, process stream fluids will not continue to contaminate the cooling waters and contaminated cooling waters are prevented from contaminating the entire system by returning to the cooling tower for recirculation. Thus, a heat exchange unit which is introducing impurities into the cooling water system can be isolated and repaired while the remainder of the system continues to operate.

It is therefore a general object of this invention to provide a method for protecting a cooling water system which continuously monitors the concentration of hydrocarbons in cooling waters flowing downstream from a heat exchange apparatus.

Another object of this invention is to provide a method for protecting a cooling water system, as aforesaid, having a hydrocarbon sensor mounted within a cooling water pipe joined to each heat exchange apparatus for monitoring hydrocarbon concentrations.

Still another object of this invention is to provide a method for protecting a cooling water system, as aforesaid, which automatically closes upstream and downstream gate valves relative to a heat exchange apparatus in which a predetermined concentration of hydrocarbons has been detected.

A further object of this invention is to provide a method for protecting a cooling water system, as aforesaid, having gate valves which can be manually opened and closed during repair or routine maintenance.

A still further object of this invention is to provide a method for protecting a cooling water system, as aforesaid, having audible and visual alarms which indicate detection of hydrocarbons and which equipment has been deactivated.

Yet another object of this invention is to provide a method for protecting a cooling water system, as aforesaid, having a sensor which can be adjusted to detect a user-determined set of hydrocarbons and concentration level.

Other objects and advantages of this invention will become apparent from the following description taken in connection with the accompanying drawings, wherein is set forth by way of illustration and example, embodiments of this invention.

DESCRIPTION OF THE PREFERRED EMBODIMENT

Figure 1:
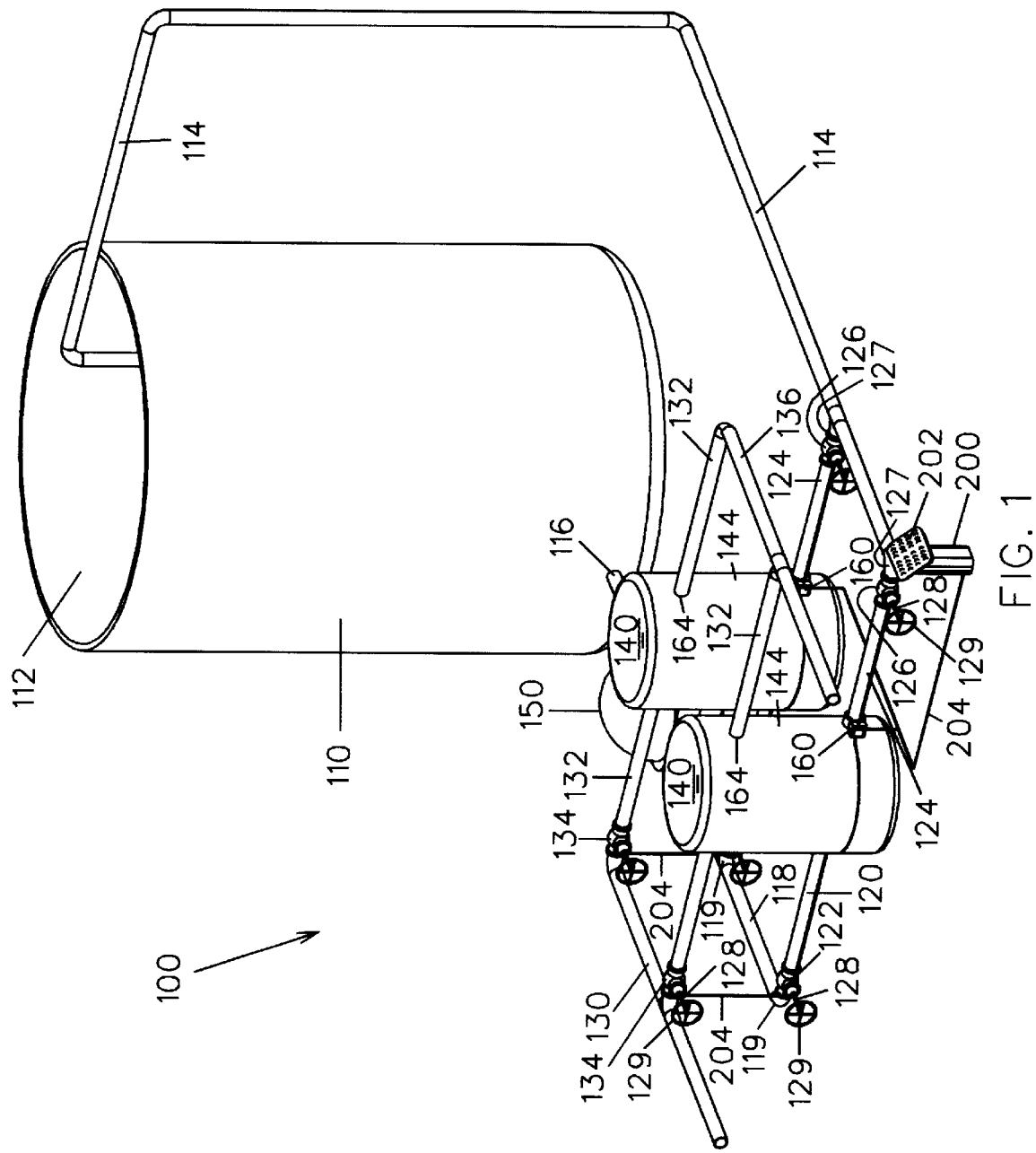
FIG. 1 is a perspective view of the cooling tower system.
Figure 2:
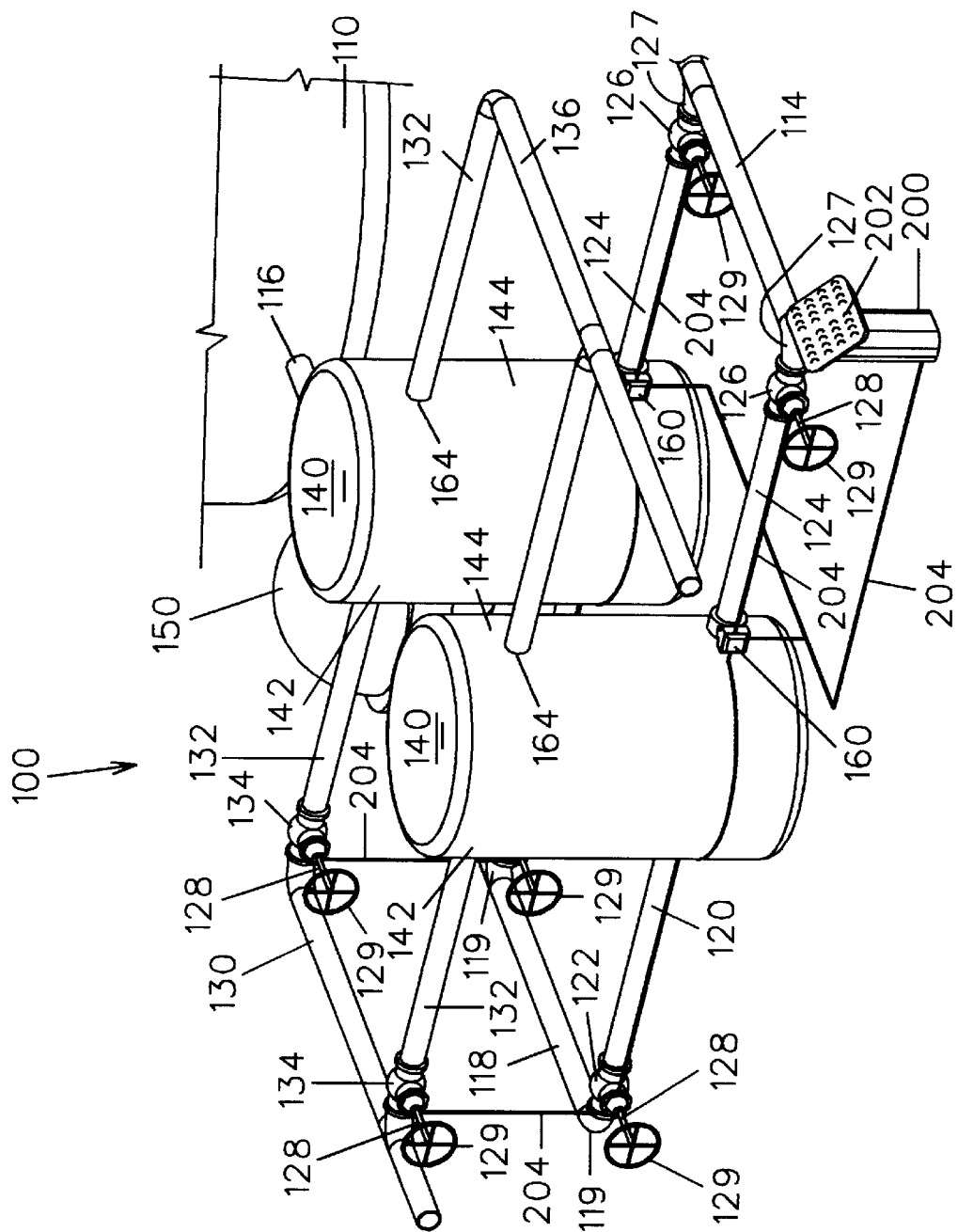
FIG. 2 is an enlarged perspective view of the cooling tower system with a portion of the cooling tower removed.
Figure 3:
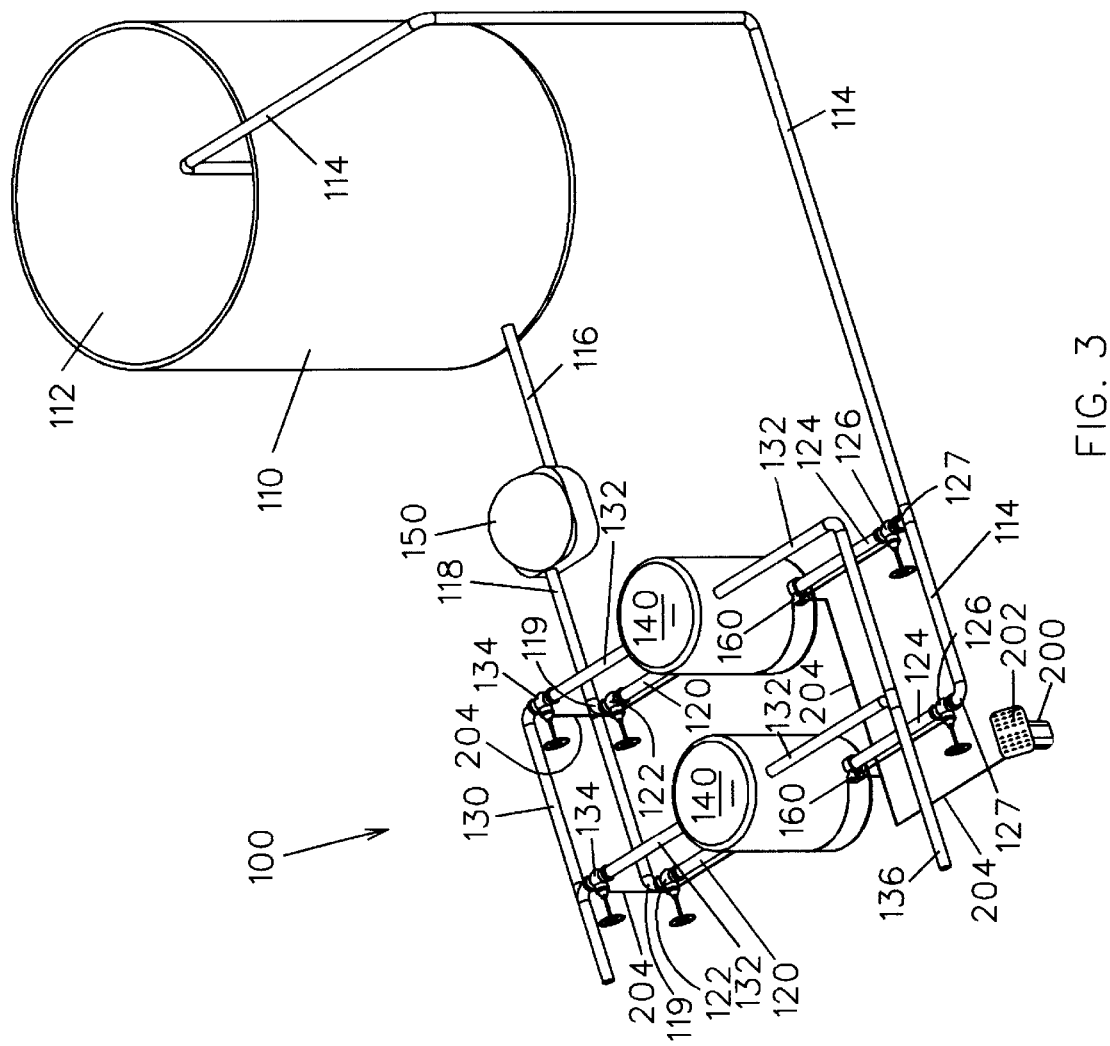
FIG. 3 is a top perspective view of the cooling tower of FIG. 1.

Turning more particularly to the drawings, FIGS. 1–3 show a cooling water system 100 which incorporates the method described herein for protecting the system 100 from damage caused by hydrocarbon impurities in cooling water. The system 100 includes a cooling tower 110 for reducing the temperature of water having become heated through an industrial heat exchange process to be further described below. The cooling tower 110 utilizes a construction and method for cooling heated water that is known in the art.

A fluid flow of a cooling solution such as water is directed through a pipe 116 from the cooling tower 110 to a circulation station 150 which pumps the fluid flow through another pipe 118 into upstream branch cooling pipes 120. Each branch cooling pipe 120 includes a gate valve 122 fixedly attached to the upstream end 119 thereof for either allowing the fluid flow to flow into the branch pipe 120 or for halting the fluid flow, the operation of the gate valves to be further described later. The system 100 further includes a pipe 130 for carrying a fluid flow of process fluids having a high temperature due to an industrial process such as the refining of a petroleum product. This process fluid pipe 130 is integrally attached to branch process pipes 132 having gate valves 134 fixedly attached thereto as described above.

Each upstream branch pipe 120, 132 is fixedly joined to an upstream end 142 of a heat exchange apparatus 140, the branch process fluid pipe 132 passing therethrough. Fluid flow from the branch cooling pipe 120 is released within the heat exchange apparatus 140 to surround the branch process fluid pipe 132, whereby heat from the hot process fluid is transferred to the cooling fluid flow. As the cooling fluid flow is warmed by heat exchange, the fluid flow is directed into a downstream branch cooling pipe 124 having a gate valve 126 integrally attached thereto near the downstream end 127 thereof. Downstream branch cooling pipes 126 are merged into a single downstream pipe 114 for returning the cooling fluid flow to the cooling tower 110 through an open upper end 112 thereof. Branch process pipes 132 carrying a fluid flow of reduced temperature are merged into a single downstream process fluid pipe 136.

A hydrocarbon sensor apparatus 160 is fixedly coupled to each downstream branch cooling pipe 124 at the junction between the outlet side 144 of a heat exchange apparatus 140 and said cooling pipe 124. Each sensor apparatus 160 includes a hydrocarbon sensor, various types of which are known, insertably mounted within each downstream branch cooling pipe 124 for monitoring the hydrocarbon concentration in the cooling fluid flow.

Figure 4:
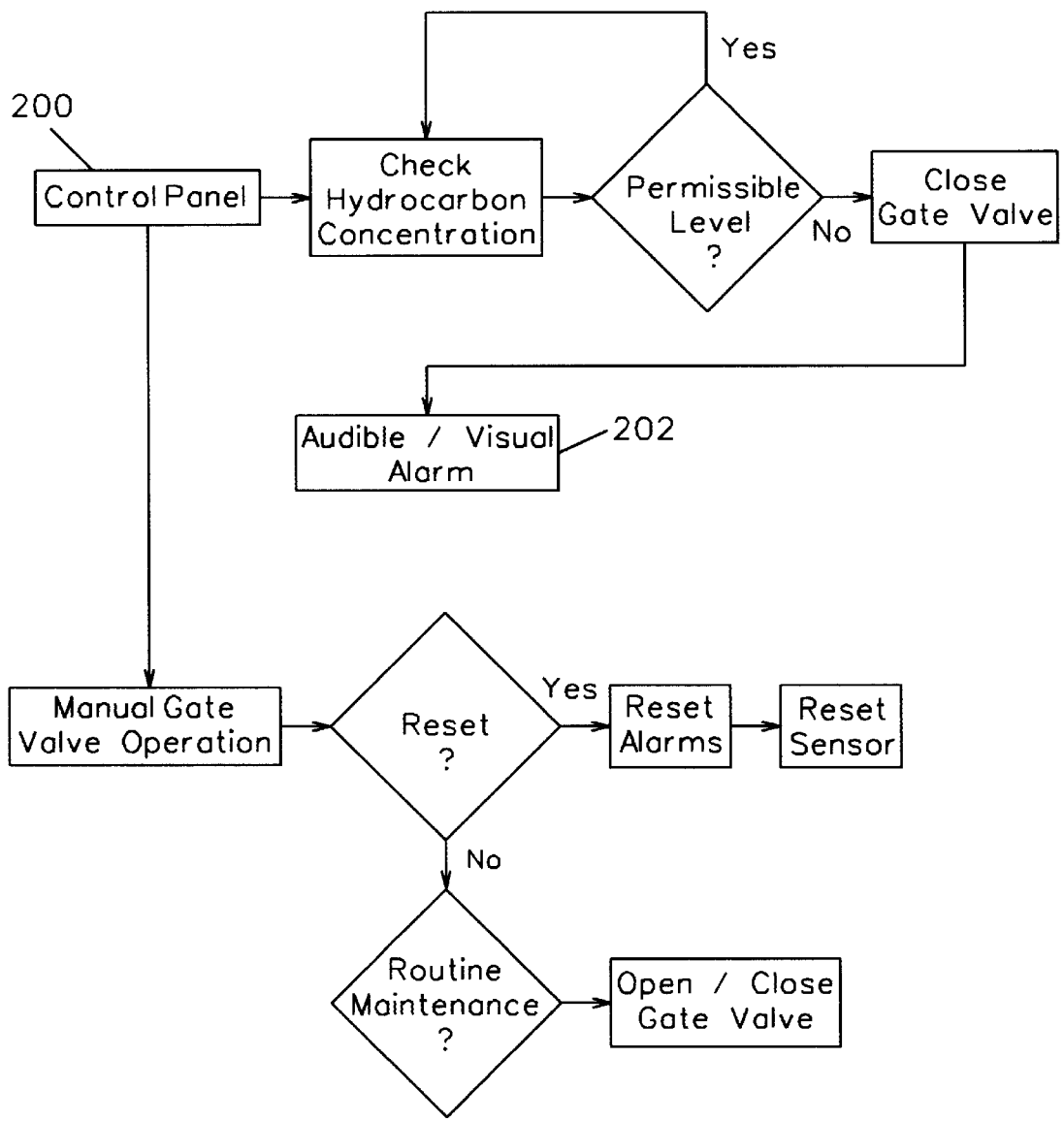
FIG. 4 is a flow chart showing the logic of the control panel.
Figure 5:
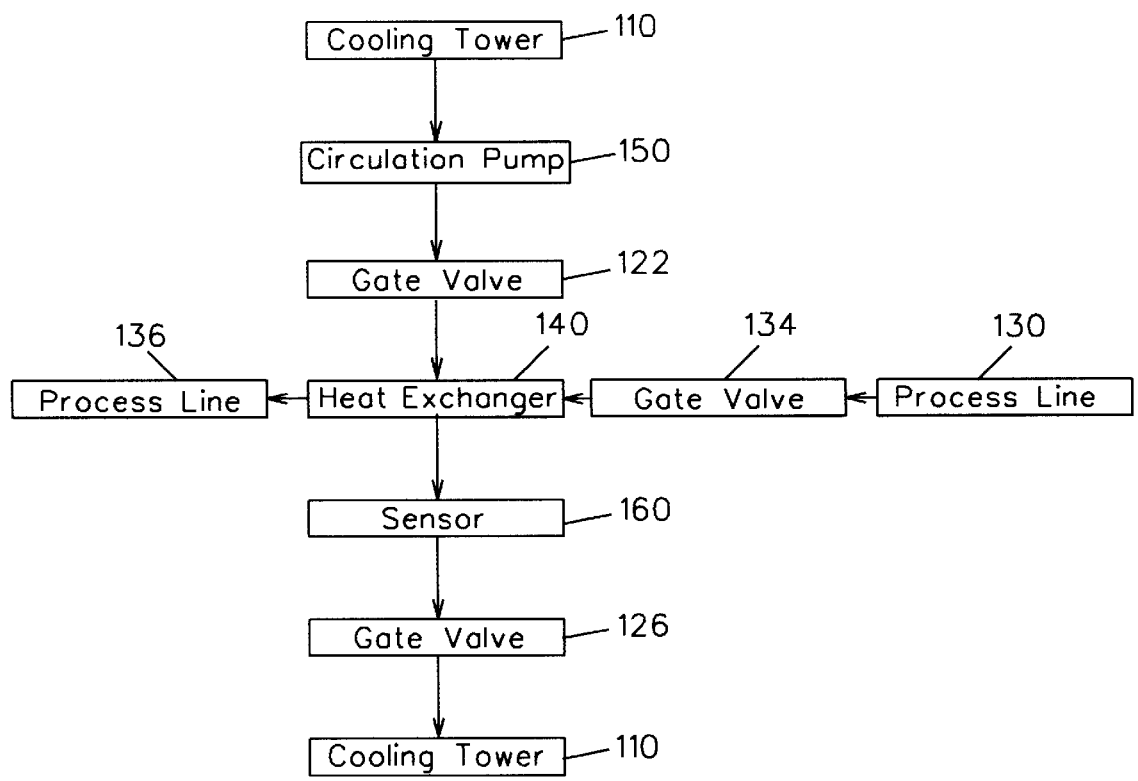
FIG. 5 is a block diagram showing the flow of the cooling fluid flow and process fluid flow.

As shown in FIG. 4, a control panel 200 provides a user-activated mode in which the hydrocarbon sensors 160 continuously monitor the hydrocarbon concentration in the downstream cooling fluid flow. If a predetermined concentration of hydrocarbons is detected as measured in parts per million, the sensor apparatus 160 sends a signal through insulated wires 204 to the control panel 200 to activate an audible alarm (not shown) and LEDs 202 which visually indicate which hydrocarbon sensor apparatus has detected an excessive hydrocarbon concentration. A signal is simultaneously sent by the sensor apparatus 160 to appropriate upstream 122 and downstream 126 branch cooling pipe gate valves and the upstream process fluid gate valve 134, the signal activating automatic closure of the valves 214. By closing upstream and downstream gate valves relative to a heat exchange apparatus 140 having a high hydrocarbon concentration indicative of process fluid leakage, continued leakage is prevented and the polluted cooling fluid flow is isolated prior to contaminating the entire system 100 through return to the cooling tower 110.

The control panel 200 further includes a mode for manual operation of the system as also shown in FIG. 4. Audible and visual alarms activated as described above can be reset if desired by a user. The signaling hydrocarbon sensor itself can also be reset to monitor the hydrocarbon concentration. In addition, the gate valves can be manually opened or closed for routine maintenance or repair purposes through user-initiated signals from the control panel. As shown in FIG. 2, each gate valve 122, 126, 134 includes a shaft 128 pivotably mounted thereto, the shaft 128 having a wheel/flange 129 integrally joined to an end thereof for opening or closing gate valves by manual rotation of the wheel/flange 129.

Accordingly, it can be seen that the method of this invention protects cooling water system equipment from scaling, fouling, and corrosion by monitoring the hydrocarbon concentration in the cooling fluid flow and by automatically initiating closure of appropriate gate valves when a predetermined hydrocarbon concentration is detected. In addition, the method sounds an audible alarm and visually indicates the source of an increased concentration of hydrocarbons which may indicate process fluid leakage.

It is understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. A method for protecting a cooling water system having a cooling tower, heat exchangers, upstream and downstream cooling pipes relative to the heat exchangers and process fluid pipes extending through the heat exchangers, the steps comprising:

continuously monitoring the hydrocarbon concentration in the downstream cooling pipes line of the cooling water system with the water flow therethrough at full speed;

identifying an excessive hydrocarbon concentration in an offending heat exchanger; and automatically closing upstream and downstream gate valves relative to the offending heat exchanger to immediately prevent contamination of non-polluted cooling water.

2. A method for protecting a cooling water system as claimed in claim 1, further comprising the step of activating an alarm indicating that an excessive hydrocarbon concentration has been detected.

3. In a cooling water system having a cooling tower, heat exchangers, upstream and downstream cooling pipes relative to the heat exchangers and process fluid pipes extending through the heat exchangers, the improvement comprising:

a control unit;

a hydrocarbon sensor electrically connected to said control unit, one said sensor mounted to each downstream cooling pipe at a junction between an end of each said cooling pipe and the corresponding heat exchanger's outlet; and a plurality of gate valves, one said gate valve mounted to each of said upstream and downstream cooling pipes and to each of said process fluid pipes, said valves electrically connected to said control unit for closure upon detection of an excessive hydrocarbon concentration by any said hydrocarbon sensors, to prevent contamination of non-polluted cooling water.

4. A cooling water system as claimed in claim 3, the improvement further comprising:

an alarm electrically connected to said control unit activated upon detection of an excessive hydrocarbon concentration.

5. A cooling water system as claimed in claim 3 wherein said gate valves include a pivotable shaft extending therefrom and having a flange integrally mounted to an end thereof for opening or closing said valves by manual rotation of said flange.

6. A method for protecting a cooling water system having a cooling tower, heat exchangers, upstream and downstream cooling pipes relative to the heat exchangers and process fluid pipes extending through the heat exchangers, the steps comprising:

selecting a threshold level of hydrocarbon concentration which may appear in an heat exchanger;

continuously monitoring the hydrocarbon concentration in the cooling water of a downstream cooling pipe relative to a heat exchanger with the water flow therethrough at full speed;

identifying a hydrocarbon concentration in said monitored pipe associated with said heat exchanger; and upon said identifying automatically ceasing the upstream and downstream flow of the cooling water through the heat exchanger to immediately prevent further contamination of non-polluted cooling water in said system.

7. A method for protecting a cooling water system as claimed in claim 6, further comprising the step of activating an alarm indicating that an excessive hydrocarbon concentration has been detected.

8. A method for protecting a cooling water system as claimed in claim 1, further comprising the steps of:

providing a gate valve in said upstream cooling pipe relative to said heat exchanger;

providing a gate valve in said downstream cooling pipe relative to said heat exchanger; and closing said gate valve upon said identifying, said closure ceasing said upstream and downstream flow through said heat exchanger.

\* \* \* \* \*

UNITED STATES PATENT AND TRADEMARK OFFICE
CERTIFICATE OF CORRECTION

PATENT NO. : 5,976,461
DATED : November 2, 1999
INVENTOR(S) : Paul R. Kostuck

Page 1 of 1

It is certified that error appears in the above-identified patent and that said Letters Patent is hereby corrected as shown below:

Column 4,
Line 33, delete "line".

Column 6,
Line 12, after "to" insert -- each --.
Line 15, after "relative" insert -- each --.
Line 18, after "said" insert -- offending --.

Signed and Sealed this

Fourth Day of September, 2001

Attest:

NICHOLAS P. GODICI
Attesting Officer
Acting Director of the United States Patent and Trademark Office